United States Patent [19]
Dutka et al.

[11] Patent Number: 5,116,402
[45] Date of Patent: May 26, 1992

[54] HERBICIDAL COMPOSITION CONTAINING DIOXOLANE, DIOXANE, OR DIOXEPANE DERIVATIVES AS ANTIDOTE

[75] Inventors: Ferenc Dutka; Tamás Komives; Katalin Fodor, née Csorba; Attila Márton; Anikó Csikós, née Glück; Éva Osztheimer, all of Budapest; Károly Henger; Róbert Laborczy, both of Balatonfüzfo; Zsuzsanna Réti, née Bosnyak; Dezső Sebok, both of Veszprém; József Szabõlcs, Balatonalmádi; Elemér Tömördi, Peremarton, all of Hungary

[73] Assignee: Magyar Tudomanvos Akademia Kozponti Kemiai Kutato Intezete Nitrokemia Inartelenek Fuzfogyartelep, Budapest, Hungary

[21] Appl. No.: 333,737

[22] Filed: Mar. 31, 1989

Related U.S. Application Data

[63] Continuation of Ser. No. 885,400, Jul. 18, 1986, abandoned, which is a continuation of Ser. No. 658,462, Oct. 9, 1984, abandoned, which is a continuation of Ser. No. 329,121, Dec. 9, 1981, abandoned.

Foreign Application Priority Data

Dec. 11, 1980 [HU] Hungary .................. 2967/80

[51] Int. Cl.⁵ .................. A01N 43/30; A01N 37/02; A01N 37/18; A01N 47/28
[52] U.S. Cl. .................. 71/88; 71/100; 71/106; 71/111; 71/118; 71/119; 71/120
[58] Field of Search .................. 71/88, 100, 106, 111, 71/118, 119, 120

[56] References Cited

U.S. PATENT DOCUMENTS

| | | | |
|---|---|---|---|
| 3,344,148 | 9/1967 | Dietrich | 71/88 |
| 3,427,326 | 2/1969 | Dietrich | 71/88 |
| 3,585,749 | 8/1970 | Chamberlin et al. | 549/347 X |
| 3,966,768 | 6/1976 | Pawloski | 549/347 |
| 4,154,595 | 5/1979 | Walker | 71/88 |
| 4,266,964 | 5/1981 | Holmsen et al. | 71/88 |
| 4,294,764 | 10/1981 | Rinehart | 260/340.9 R |
| 4,322,240 | 3/1982 | Teach | 71/88 |
| 4,400,197 | 8/1983 | Rinehart | 71/88 |
| 4,406,686 | 9/1983 | Walker | 71/88 |

OTHER PUBLICATIONS

Thomson, Agricultural Chemicals, Book II Herbicides, pp. 73-75 (1983-1984 revision).
Steinbeck, Karl, "Synthese von 2-Dihalogenmethyl-1,-3-dioxolanen und 2-Dihalogenmethyl-1,3-dioxanen." Chem. Berichte 112:2402-2412 ('79).

*Primary Examiner*—Richard L. Raymond
*Assistant Examiner*—S. Mark Clardy
*Attorney, Agent, or Firm*—Keil & Weinkauf

[57] ABSTRACT

The invention relates to a herbicidal composition which contains, besides binding, wetting, dispersing, emulsifying agents, solvents and/or surface-active substances, herbicides as active agent of thiocarbamate, carbamate, acid amide or urea type alone or in a combination, furthermore as antidote a compound of the general formula I

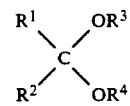

wherein
  $R^1$ and $R^2$, independently of each other, are hydrogen, $C_{1-6}$alkyl, $C_{2-6}$alkenyl, $C_{1-4}$cyanoalkyl, $C_{1-6}$haloalkyl, phenyl-$C_{1-4}$-haloalkyl, phenyl, halogenphenyl, $C_{1-4}$-alkyl-phenyl, $C_{1-4}$-alkoxyphenyl, furfuryl;
  $R^3$ and $R^4$, independently of each other, are hydrogen, $C_{1-18}$-alkyl, $C_{2-4}$-haloalkyl, $C_{2-4}$-cyanoalkyl, $C_{1-4}$-alkoxy-$C_{2-4}$-alkyl, $C_{5-6}$-cycloalkyl, phenyl-$C_{1-4}$-alkyl, $C_{3-4}$-alkenyl, phenyl-$C_{3-4}$-alkenyl, di-$C_{1-4}$-alkylamino-$C_{2-4}$-alkyl, hydroxy-$C_{2-6}$-alkyl, furfuryl, tetrahydrofurfuryl, $C_{1-4}$-alkoxy-$C_{2-4}$-alkoxy-$C_{2-4}$-alkyl;
  $R^3$ and $R^4$, together, are $C_{2-4}$-alkylene, $C_4$-alkenylene, glucofuranosylene, acetoxy-$C_3$-alkylene, $C_{1-4}$-alkoxy-$C_3$-alkylene, hydroxy-$C_3$-alkylene, halogen-$C_3$-alkylene; wherein the quantity of the antidote lies between 0.01 and 15 parts by weight referred to 1 part by weight of herbicidal agent, furthermore the composition contains altogether 0.1 to 95 percent by weight of the herbicidal agents and the antidote.

33 Claims, No Drawings

HERBICIDAL COMPOSITION CONTAINING DIOXOLANE, DIOXANE, OR DIOXEPANE DERIVATIVES AS ANTIDOTE

This application is a continuation of application Ser. No. 885,400, filed on Jul. 18, 1986, which is a continuation of Ser. No. 658,462, filed on Oct. 9, 1984, which is a continuation of Ser. No. 329,121, filed Dec. 9, 1981, all abandoned.

The invention relates to herbicidal compositions containing aldehyde and ketone derivatives as antidotes as well as to the use of these antidotes for the prevention of damage to cultivated plants caused by herbicidal agents.

For the more effective use of the herbicides an increase in selectivity is necessary. Numerous herbicidal agents available on the market when used alone or in combination with other herbicidal agents are toxic to very different weeds in concentrations depending on the resistance of the weed. Their economical use, however, is restricted and hindered, respectively, by the fact that when using them in such concentrations the cultivated plant also is damaged. The damage to the cultivated plant and its irregular development can lead to a significant decrease in crop yields. This damaging effect can be moderated, and perhaps eliminated with the help of herbicidal antidotes. Such antidotes and their use are disclosed in the Hungarian patents Nos. 165,736, 173,775 and 174,487. The chemical character of the compounds described in these patent applications fundamentally differs from that of the compounds of the present invention. Further, in contrast to the antidotes described earlier which showed a positive effect only on a rather limited number of herbicide—cultivated plant combinations—the harmful effect of some herbicides on cultivated plants can be decreased significantly if the seed of the cultivated plant is treated with an antidote of the following formula I before planting/sowing or if the antidote is added to the soil,

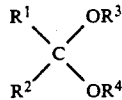

wherein
$R^1$ and $R^2$, independently of each other, are hydrogen, $C_{1-6}$ alkyl, $C_{2-6}$ alkenyl, $C_{1-4}$ cyanoalkyl, $C_{1-6}$-haloalkyl, phenyl-$C_{1-4}$-haloalkyl, phenyl, halogenphenyl, $C_{1-4}$-alkylphenyl, $C_{1-4}$-alkoxyphenyl, furfuryl;
$R^3$ and $R^4$, independently of each other, are hydrogen, $C_{1-18}$-alkyl, $C_{2-4}$-haloalkyl, $C_{2-4}$-cyanoalkyl, $C_{1-4}$-alkoxy-$C_{2-4}$-alkyl, $C_{5-6}$-cycloalkyl, phenyl-$C_{1-4}$-alkyl, $C_{3-4}$-alkenyl, phenyl-$C_{3-4}$-alkenyl, di-$C_{1-4}$-alkylamino-$C_{2-4}$-alkyl, hydroxy-$C_{2-6}$-alkyl, furfuryl, tetrahydrofurfuryl, $C_{1-4}$-alkoxy-$C_{2-4}$-alkoxy-$C_{2-4}$-alkyl;
$R^3$ and $R^4$, together, are $C_{2-4}$-alkylene, $C_4$-alkenylene, glucofuranosylene, acetoxy-$C_3$-alkylene, $C_{1-4}$-alkoxy-$C_3$-alkylene, hydroxy-$C_3$-alkylene, halogen-$C_3$-alkylene.

Among these substituents the alkyl group can be straight-chain or branched-chain, the haloalkyl can contain 1 to 4 fluorine, chlorine or bromine atoms, the cyanoalkyl group contains at least a cyano group, the alkyl group can be substituted by a halogen atom, a haloalkyl, alkoxy or alkyl group once or more times.

According to the invention the herbicidal compositions contain the compound of the above formula I—wherein the meanings of $R^1$ to $R^4$ are as defined above—as antidote and herbicidal agent(s); the composition contains 0.01 to 15 parts by weight of the antidote per 1 part by weight of herbicidal agent and consists of 0.1 to 95 percent based on the active agents of the composition. The compositions can be used for the detoxication of thiocarbamate herbicides, such as EPTC (S-ethyl-N,N-di-n-propyl-thiocarbamate), Butylate (S-ethyl-N,N-di-isobutyl-thiocarbamate), Vernolate (S-n-propyl-N-,N-di-n-propyl-thiocarbamate), Pebulate (S-n-propyl-N-butyl-N-ethyl-thiocarbamate), Molinate (S-ethyl-N,N-hexamethylene-thiocarbamate), Cycloate (S-ethyl-N-ethyl-N-cyclohexyl-thiocarbamate), Diallate (S-2,3-dichloro-ally-N,N-di-isopropyl-thiocarbamate), further on of carbamates, such as Barban (4-chloro-2-butinyl-N-/3-chloro-phenyl/-carbamate), of amides, such as Acetochlor (2-ethyl-6-methyl-N-ethoxy-methyl-chloro-acetanilide), Alachlor (2,6-diethyl-N-methoxy-methyl-chloro-acetanilide), Metolachlor (6-ethyl-2-methyl-N-/2-methoxy-1-methyl-ethyl/-chloro-acetanilide) and of carbamide derivatives, such as Linuron (3-/3,4-dichloro-phenyl/-1-methoxy-1-methyl-urea).

Independently from any concrete effect mechanism the advantage of the aldehyde and ketone derivatives of the invention resides in the moderating or eliminating of the harmful effect of the herbicides on cultivated plants without decreasing the weed control effect.

The compounds of the above general formula can be prepared by different methods depending on their character according to the following examples.

The synthesis of the compounds of the formula I can be carried out as follows: an oxo compound of the formula II

wherein $R^1$ and $R^2$ are as defined in formula I is admixed with a corresponding mono- or di-alcohol, respectively, in benzene in stoichiometric ratio and it is refluxed for several (4 to 11) hours. The formed water is continuously removed from the system (with a Dean-Stark apparatus). As catalyst preferably 4-methyl-benzenesulphonic acid is used for the preparation. The reaction product is separated by filtration or distillation depending on its character.

The compounds of the formula I can also be prepared from compounds of the formula III

wherein $R^1$ and $R^2$ are as defined in the formula I, $R^5$ and $R^6$, however, stand for a $C_{1-4}$ alkyl group being identical or different, so that any of them is reacted with a corresponding mono- or bivalent alcohol, in the presence of a catalyst, e.g. 4-methyl-benzene-sulphonic acid, at reflux temperature. The product can be separated according to the method mentioned before.

Literature references mention different special and general methods of preparing compounds of the general formulas II and III, e.g.:

Houben-Weyl: *Methoden der organischen Chemie*, IV. edition, Gerog Thieme Verlag, Stuttgart, volume V/3 (1962), pages 611–12, 616, 619; volume V/4 (1960), pages 163–170, 173, 175–182; volume VI/3 (1965), pages 250–2, 256–9, 275–8, 286.

*Ullmanns Encyklopadie der technischen Chemie*, Urban and Schwarzenberg, Munchen-Berlin, 3rd edition (1954), volume 5, page 319.

D. P. Kaufman: *J. Org. Chem.* 29, 1956–60 (1964).

The following examples serve the illustration of the essence of the invention without limiting the scope of the invention to these examples.

EXAMPLE 1

Preparation of dichloro-acetaldehyde diethyl-acetal

Into 95% ethanol kept at 25° chlorine gas is led until two phases are formed. The organic phase is dried on calcium carbonate, then distilled.

Boiling point: 107°–108° C./Hgmm

EXAMPLE 2

Preparation of 2,3-dibromo-propionaldehyde diethyl-acetal 7 g of 1,2-dibromo-propionaldehyde are added to a mixture of 5 g of ortho-formic acid triethyl-ester and 10 ml of ethanol. The solution is refluxed for 2 hours, remains standing for a night, then it is vacuum-distilled.

Boiling point: 107° to 108° C./11 Hgmm.

EXAMPLE 3

Preparation of trichloro-acetaldehyde diamyl-acetal

A mixture of 5 g of chloral-hydrate, 10 ml of amyl-alcohol, 0.1 g of 4-methyl-sulphonic acid and 50 ml of benzene is kept at reflux temperature and the formed water is separated by means of a Dean-Stark apparatus. After a reaction time of 9 hours the benzene is washed with a sodium hydrogen carbonate solution and water, dried on magnesium sulfate, then it is vacuum-distilled.

$n_D^{20}$: 1.4549.

EXAMPLE 4

Preparation of dichloro-acetaldehyde dimethyl-acetal

A mixture of 8 g of dichloro-acetaldehyde diethyl-acetal, 30 ml of methanol and 0.1 g of 4-methyl-benzene-sulphonic acid is kept at reflux temperature for 5 hours, then distilled.

Boiling point: 167°–168° C.

EXAMPLE 5

Preparation of trichloro-acetaldehyde diheptyl-acetal

A mixture of 5 g of chloral hydrate, 12 g of heptanol, 0.1 g of 4-methyl-benzene-sulphonic acid and 50 ml of benzene is kept at reflux temperature and the formed water is separated by means of a Dean-Stark apparatus. Afater a reaction time of 9 hours the benzene is washed with a sodium hydrogen carbonate solution and water, dried on magnesium sulfate, then vacuum distilled.

$n_D^{20}$: 1.4573.

EXAMPLE 6

Preparation of 2-trichloromethyl-1,3-dioxane 21.6 g of chloral hydrate are admixed with 9.6 g of propylene-glycol, then 16.8 ml of concentrated sulphuric acid are added. It is heated at 60°–70° C. for two hours and after dilution with 60 ml of water it is extracted two times with 60 ml of chloroform. The chloroformic phase is washed with water and sodium hydrogen carbonate, dried on magnesium sulfate, then the product is vacuum distilled after distilling off the chloroform.

Boiling point: 98° C./9 Hgmm.

EXAMPLE 7

Preparation of trichloro-acetaldehyde di-isoamyl acetal

A mixture of 5 g of chloral-hydrate, 10 g of isoamyl-alcohol, 0.1 g of 4-methyl-benzene-sulphonic acid and 50 ml of benzene is kept at reflux temperature and the formed water is separated by means of a Dean-Stark apparatus. After a reaction time of 9 hours the benzene is washed with a sodium-hydrogen-carbonate solution and water, dried on magnesium sulfate, then vacuum distilled.

$n_D^{20}$: 1.4519.

EXAMPLE 8

Preparation of trichloro-acetaldehyde dimethyl-acetal 5 g of chloral hydrate, 30 ml of absolute methanol and 2.5 ml of concentrated sulphuric acid are kept at reflux temperature for 10 hours, then the reaction mixture is distilled.

Boiling point: 175°–176° C.

EXAMPLE 9

Preparation of trichloro-acetaldehyde-dibutyl-acetal

Into an apparatus supplied with a Dean-Stark water separator 7 g of chloral hydrate, 10 g of butyl alcohol, 0.1 g of 4-methyl-benzene-sulphonic acid and 50 ml of benzene are weighed. The mixture is heated on a water-bath and the water separation is continued for 10 hours. The benzene is washed with water and sodium hydrogen carbonate, then distilled off and the product is vacuum distilled.

Boiling point: 104°–105° C./3 Hgmm.

EXAMPLE 10

Preparation of 2-dichloro-methyl-1,3-dioxane 9 g of dichloro-acetaldehyde diethyl-acetal and 5 g of propylene glycol are heated on a water-bath in the presence of 0.1 g of 4-toluene-sulphonic acid for 4 hours. The product is cleaned by vacuum distillation in the presence of 0.3 g of potassium carbonate.

Boiling point: 78°–79° C./15 Hgmm.

EXAMPLE 11

Preparation of 2-(trichloro-methyl)-4-(hydroxymethyl)-dioxolane

A mixture of 16 g of chloral, 5 g of glycerine and 5 ml of concentrated sulphuric acid is,heated on a water-bath for 10 hours, then the reaction mixture is distilled in vacuo.

Boiling point: 162°–164° C.

EXAMPLE 12

Preparation of trichloro-acetaldehyde-methyl-butyl-acetal 4 g of butyl alcohol, 0.1 g of 4-methyl-benzene-sulphonic acid and 50 ml of benzene are added to 10 g of 1-methoxy-2,2,2-trichloro-ethanol. The water separation is continued in a Dean-Stark apparatus for 10 hours while heating the mixture on a water-bath. The benzene is washed with water and the aqueous solution of sodium hydrogen carbonate, dried on magnesium sulfate, distilled off and the product is cleaned by distillation in vacuo.

Boiling point: 77°–78° C./4 Hgmm.

EXAMPLE 13

Preparation of bromoacetaldehyde diethyl-acetal

To a mixture of 10 g of vinyl acetate and 20 ml of carbon tetrachloride under cooling (temperature 10° C.) 10 ml of carbon tetrachloride and 18.5 g of bromide solution are added. 60 ml of ethanol are added to the mixture and it remains standing for 2 days. The organic phase is washed twice with 50 ml of water, then it is distilled in vacuo.

Boiling point: 59°–61° C./15 Hgmm.

EXAMPLE 14

Preparation of trichloro-acetaldehyde dihexyl-acetal

A mixture of 5 g of chloral hydrate, 11 g of hexanol, 0.1 g of 4-methyl-benzene-sulphonic acid and 50 ml of benzene is kept at reflux temperature and the formed water is separated by means of a Dean-Stark apparatus. After a reaction time of 9 hours the benzene is washed with a sodium hydrogen carbonate solution and water, dried on magnesium sulfate, then distilled in vacuo.

$n_D^{20}$: 1.4562.

EXAMPLE 15

Preparation of cyan-acetaldehyde diethyl-acetal

A mixture of 8 g of bromo-acetaldehyde diethyl-acetal, 3 g of sodium-cyanide and 20 ml of dimethyl-sulfoxide is admixed at a temperature of 80° C. for 5 hours. The reaction mixture is poured on 80 ml of water, then twice extracted with 50 ml of chloroform. The chloroform extract is washed twice with 30 ml of water, dried on magnesium sulfate, then distilled in vacuo.

Boiling point: 97°–98° C./10 Hgmm.

EXAMPLE 16

Preparation of dichloro-acetaldehyde dipropyl-acetal

A mixture of 5 g of dichloro-acetaldehyde diethyl-acetal, 30 ml of propanol and 0.1 g of 4-methyl-benzene-sulphonic acid is heated on a water-bath for 5 hours, then distilled.

Boiling point: 210°–211° C.

EXAMPLE 17

Preparation of trichloro-acetaldehyde diethyl-acetal 5 g of chloral-hydrate, 40 ml of absolute ethanol and 2.5 ml of concentrated sulphuric acid are kept on reflux temperature for 10 hours, whereupon the reaction mixture is distilled.

Boiling point: 190°–192° C.

EXAMPLE 18

Preparation of 2-dichloromethyl-1,3-dioxolane 10 g of dichloroacetaldehyde diethyl-acetal and 3 g of ethylene-glycol are heated in the presence of 0.1 g of 4-methyl-benzene-sulphonic acid on a water-bath for 5 hours, whereupon the product is distilled in vacuo.

Boiling point: 187° C.

EXAMPLE 19

Preparation of dichloro-acetaldehyde didodecyl-acetal

A mixture of 5 g dichloro-acetaldehyde diethyl-acetal, 30 g of dodecanol and 0.1 g of 4-methyl-benzene-sulphonic acid is heated on a water-bath for 5 hours, then distilled.

$n_D^{20}$: 1.4783.

EXAMPLE 20

Preparation of dichloro-acetaldehyde dioctyl-acetal

A mixture of 5 g of dichloro-acetaldehyde diethyl-acetal, 25 g of octanol and 0.1 g of 4-methyl-benzene-sulphonic acid is heated on a water-bath for 5 hours, then distilled.

$n_D^{20}$: 1.4627.

EXAMPLE 21

Preparation of 2-(dichloro-methyl)-6-(acetoxy-methyl)-dioxolan

A mixture of 5 g of 2-(dichloro-methyl)-4-(hydroxy-methyl)-dioxolan, 20 ml of acetic acid anhydride and 1 ml of concentrated sulphuric acid is heated on a water-bath for 1 hour, then distilled in vacuo.

Boiling point: 181°–183° C./19 Hgmm.

EXAMPLE 22

Preparation of 2-(dichloro-methyl)-4-(hydroxy-methyl)-dioxolan

To a mixture of 5.5 g of 2-(trichloro-methyl)-4-(hydroxy-methyl)-dioxolan and 30 ml of acetic acid under stirring 1.6 g of zinc dust are added within 30 minutes. After a further 15 minutes of stirring the reaction mixture is distilled.

Boiling point: 156°–157° C./19 Hgmm.

EXAMPLE 23

Preparation of 2-(trichloro-methyl)-4-(methoxy-methyl)-dioxolan

A mixture of 5.5 g of 2-(trichloro-methyl)-4-hydroxy-methyl)-dioxolan, 3 g of dimethyl-sulfate, 3 g of potassium carbonate and 30 ml of water is admixed at room temperature for 4 hours. The mixture is extracted twice with 30 ml of chloroform, the extract is washed with 50 ml of water, then distilled.

Boiling point: 153°–155° C./18 Hgmm.

EXAMPLE 24

Preparation of dichloro-acetaldehyde ethyl-hemi-acetal

A mixture of 6.1 g of dichloro-acetaldehyde, 2.3 g of ethanol and 15 ml of benzene is left standing for a night, then distilled.

Boiling point: 109°–110° C.

EXAMPLE 25

Preparation of 2,2,2-trichloro-1-(ethoxy-ethoxy)-ethanol

A mixture of 7 g of chloral, 4.8 g of ethylene-glycol monoethyl-ether and 15 ml of benzene is left standing for a night at room temperature, then distilled.

$n_D^{20}$: 1.4697.

EXAMPLE 26

Preparation of 2,2,2-trichloro-1-allyloxy-ethanol

A mixture of 7 g of chloral, 2.9 of allyl-alcohol and 15 ml of benzene is left standing for a night at room temperature, then distilled.

$n_D^{20}$: 1.4820.

EXAMPLE 27

Preparation of chloro-acetaldehyde dimethyl-acetal

To a mixture of 5 g of vinyl acetate and 20 ml of methanol acetone cooled on dry ice 5 g of dry chlorine gas are added, then it is left standing for a night at room temperature. The reaction mixture is then poured onto 50 g of ice-water. The product is extracted with 30 ml of chloroform, the extract is washed with sodium hydrogen carbonate solution and water, then dried on magnesium sulfate and distilled.

Boiling point: 53°–54° C./16 Hgmm.

EXAMPLE 28

Preparation of chloro-acetaldehyde diethyl-acetal

To a mixture of 5 g of vinyl acetate and 27 ml of ethanol acetone cooled on dry ice 5 g of dry chlorine gas are added, then it is left standing for a night at room temperature. The reaction is poured onto 50 g of ice-water. The product is extracted with 30 ml of chloroform, the extract is washed with a sodium hydrogen carbonate solution and water, then dried on magnesium sulfate and distilled.

Boiling point: 53°–54° C./16 Hgmm.

EXAMPLE 29

Preparation of α-chloralose

A mixture of 4.5 g of glucose, 19 g of chloral, 20 ml of chloroform and 0.05 g of 4-methyl-benzene-sulphonic acid is kept at reflux temperature for 7 hours and the formed water is separated by means of a Dean-Stark apparatus. The solvent is distilled off and the residue is kept at 60° C. for 20 minutes. The sedimented material is filtrated and the pH value of the mother lye adjusted to 6.5 with sodium hydroxide. The separated precipitate is filtered.

Melting point: 182°–183° C.

EXAMPLE 30

Preparation of β-chloralose

Under stirring 0.05 g of 4-methyl-benzene sulphonic acid and 20 ml of chloroform are added to a mixture of 4.5 g of glucose and 19 g of choral. The mixture is heated to reflux temperature and the formed water is separated by means of a Dean-Stark apparatus. The solvent is distilled off, then the mixture is kept at a temperature of 60° C. for 20 minutes. The separated material is filtered off.

Melting point: 231°–232° C.

EXAMPLE 31

Preparation of 2-(dibromo-methyl)-dioxolan

A mixture of 5.3 g of dibromo-acetaldehyde diethyl-acetal, 7 g of ethylene glycol and 0.05 g of 4-methyl-benzene sulphonic acid is heated on a water-bath for 7 hours, then distilled in vacuo.

Boiling point: 102°–103° C./9 Hgmm.

EXAMPLE 32

A mixture of 4.5 g of 1,1-dichloro-acetone, 3.7 ml of ethylene glycol, 0.1 g of 4-methyl-benzene-sulphonic acid and 30 ml of benzene is kept at reflux temperature for 9 hours while continuous water separation. The reaction mixture is washed with a sodium hydrogen carbonate solution, dried on magnesium sulfate and distilled.

Boiling point: 92°–94° C./27 Hgmm.

EXAMPLE 33

Preparation of 2-chloromethyl-dioxan

A mixture of 4.7 g of chloro-acetaldehyde diethyl-acetal, 9 g of propylene glycol and 0.05 g of 4-methyl-benzene-sulphonic acid is heated for 9 hours on a water-bath, then distilled in vacuo.

Boiling point: 71°–74° C./14 Hgmm.

EXAMPLE 34

Preparation of 2-(dichloro-methyl)-2-phenyl-1,3-dioxolan

A mixture of 6 g of 1,1-dichloro-acetophenon, 3.8 ml of ethylene glycol, 0.1 g of 4-methyl-benzene-sulphonic acid and 40 ml of benzene is kept at reflux temperature for 11 hours and the formed water is continously separated by means of a Dean-Stark apparatus. The reaction mixture is washed with a sodium carbonate solution, dried on magnesium sulfate and evaporated. The formed solid material is recrystallized from hexane.

Melting point: 59°–60° C.

EXAMPLE 35

Preparation of 2-(bromo-methyl)-dioxolan 4.3 of bromo-acetaldehyde diethyl-acetal are heated in the presence of 10 g of ethylene glycol and 0.05 g of 4-methyl-benzene-sulphonic acid for 8 hours on a water-bath, whereupon the reaction mixture is distilled.

Boiling point: 173°–174° C.

EXAMPLE 36

Preparation of bromo-acetaldehyd

Into 80 ml of carbon tetrachloride solution of 43 g of vinyl acetate cooled with ice 60 ml of carbon tetrachloride solution of 80 g of bromide are dropped so that the reaction mixture temperature does not rise above +10° C. Then the reaction mixture is dropped to 3.8 mol of allyl alcohol cooled with salty ice at a temperature under +10° C. After two-day standing the carbon tetrachloride phase is washed with water, dried on anhydrous sodium sulfate and after the evaporation of the solvent the obtained residue is distilled fractionally.

Boiling point: 80°–82° C./1 Hgmm, yield: 72.1%

EXAMPLE 37

Preparation of 2-dichloromethyl-2-methyl-1,3-dioxolan 8.0 g of 1,1-dichloroacetone are reacted with 6.7 ml of ethylene-glycol in the presence of p-toluene-sulphonic acid catalyst in a water-separating system or by means of a water binding molecule-screen /Å 4/, finally it is distilled/on a Vigreux column/.

Boiling point: 93°–94° C./2 Hgmm.

Preparation of 1,1-dichloroacetone used as starting material:

To 14.5 g of acetone weighed into a round-bottom flask provided with a reflux condenser linked with- /CaCl₂ tube, a dropping funnel /and a mixer, and 67.5 g of sulfuryl-chloride are dropped while cooling at such a speed that the temperature of the system does not rise above 30°-40° C.; after a postreaction of 3 to 5 hours the residue of the reagent is removed by distillation.

Boiling point: 117°-118° C.

EXAMPLE 38

Preparation of 2-bromo-propionaldehyde-diethyl-acetal 13.22 g of propion-aldehyde-diethyl-acetal are dissolved in 15 ml of carbon tetrachloride; at −10° C. 20 ml of the carbon tetrachloride solution of 17.58 g of bromide are dropped to it under stirring. After its warming to room temperature it is distilled in vacuo.

Boiling point: 79°-80° C./20 Hgmm.

With the processes disclosed in the previous examples in detail from the corresponding starting substances numerous further compounds of the formula

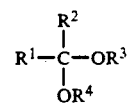

/1/ were prepared which can be used well as antidotes in the herbicidal compositions according to the invention. These compounds with the indication of the substituents in positions $R^1$, $R^2$, $R^3$ and $R^4$, are summarized in Table I wherein the individual compounds are given a serial number and in the further part of the specification the antidotes are mentioned under these numbers.

TABLE I

| Number of the compound | $R^1$ | $R^2$ | $R^3$ | $R^4$ | Boiling Point (°C.) Melting Point (°C.) |
|---|---|---|---|---|---|
| 1 | H | —CHCl₂ | —C₅H₁₁ | —C₅H₁₁ | 98–100° C./30 mm Hg |
| 2 | H | —CHCl₂ | cyclo-pentyl | cyclo-pentyl | 105–110° C./1 |
| 3 | —CHCl₂ | —CH₃ | —CH₂—CH₂— | | $n_D^{25}$ 1.4671; 93–94° C./27 |
| 4 | H | —CHCl₂ | 2-bromo-ethyl | 2-bromo-ethyl | 129–130° C./5 |
| 5 | —CHBr₂ | H | —C₂H₅ | —C₂H₅ | 195–200° C. |
| 6 | H | —CHCl₂ | —C₆H₁₃ | —C₆H₁₃ | 120–122° C./38 |
| 7 | H | —CHCl₂ | 2-methoxy-ethoxy-ethyl | 2-methoxy-ethoxy-ethyl | $n_D^{25}$ 1.4427 |
| 8 | H | —CHCl₂ | —C₁₂H₂₅ | —C₁₂H₂₅ | $n_D^{20}$ 1.4788 |
| 9 | CH₂BrCHBr— | H | —C₂H₅ | —C₂H₅ | 107–108° C./11 |
| 10 | —CHCl₂ | H | i-C₃H₇ | i-C₃H₇ | 212–214° C. |
| 11 | furyl | H | —C₂H₅ | —C₂H₅ | 189–191° C. |
| 12 | —CHCl₂ | H | —CH/CH₃/—CH₂— | | 90–93° C./10 |
| 13 | H | H | —CH₃ | —CH₃ | b.p. 41–42° C. |
| 14 | —CHCl₂ | H | —CH₂—CH=CH—CH₂— | | 110° C./10 |
| 15 | C₆H₅—CHBrCHBr— | H | —C₂H₅ | —C₂H₅ | 152–154° C./12 |
| 16 | 2-chloro-phenyl | H | —C₂H₅ | —C₂H₅ | 124–126° C./16 |
| Number of the compound | $R^1$ | $R^2$ | $R^3$ | $R^4$ | Boiling point (°C.) $n_D^{20}$ |
| 17 | —CCl₃ | H | —CH₃ | —C₂H₅ | 193–194° C. |
| 18 | —CHCl₂ | H | —CH/CH₃/—/CH₂/₂— | | 82–84° C./15 |
| 19 | —CHCl₂ | H | —CH₃ | —CH₃ | 167–168° C. |
| 20 | H | —CHCl₂ | benzyl | benzyl | 176–178° C./5 |
| 21 | —CH₂CN | H | —C₂H₅ | —C₂H₅ | 97–98° C./10 |
| 22 | —CHCl₂ | H | i-C₄H₉ | i-C₄H₉ | 88–90° C./30 |
| 23 | H | —CHCl₂ | 2-methyl-butyl | 2-methyl-butyl | 137–139° C./38 |
| 24 | H | —CHCl₂ | 2-methoxy-ethyl | 2-methoxy-ethyl | 126–128° C./28 |
| 25 | —CH₃ | H | —C₂H₅ | —C₂H₅ | 101–103° C. |
| 26 | CH₃CHBrCHBr— | H | —C₂H₅ | —C₂H₅ | 113–134° C./13 |
| 27 | H | —CHCl₂ | tetrahydrofurfuryl | tetrahydrofurfuryl | |
| 28 | —CHCl₂ | H | —CH₂—CH₂— | | 69–72° C./9 |
| 29 | —CHCl₂ | H | crotyl | crotyl | $n_D$ 1.4981 |
| 30 | vinyl | H | —C₂H₅ | —C₂H₅ | 89–90° C. |
| 31 | 4-methyl-phenyl | H | —C₂H₅ | —C₂H₅ | 116–119° C./112 |
| 32 | —CHCl₂ | H | —CH₂—CH₂— | | 106–108° C./7 |
| 33 | —CHCl₂ | H | allyl | allyl | 61–63° C./1.5 |
| 34 | H | —CHCl₂ | —C₂H₅ | H | 109–110° C. |
| 35 | —CHCl₂ | H | —CH/C₂H₅/—CH₂— | | 63–65° C./2 |
| 36 | H | —CHCl₂ | sec.i-butyl | sec.i-butyl | 84–86° C./30 |
| 37 | H | —CHCl₂ | —CH₂—C≡CH | —CH₂—C≡CH | $n_D$ 1.4860 |
| 38 | —CH₂Br | H | —C₂H₅ | —C₂H₅ | 59–61° C./19 |
| 39 | —CH₂Cl | H | —C₂H₅ | —C₂H₅ | 53–54° C./16 |
| 40 | H | —CHCl₂ | furfuryl | furfuryl | $n_D$ 1.5372 |
| 41 | —CCl₃ | H | —C₂H₅ | —C₂H₅ | 84–85° C./10 |
| 42 | —CHCl₂ | H | —C₄H₉ | —C₄H₉ | 57–60° C./1 |
| 43 | H | —CHCl₂ | 1-methyl-n-heptyl | 1-methyl-n-heptyl | $n_D$ 1.4621 |
| 44 | H | —CHCl₂ | 2-chloro-ethyl | 2-chloro-ethyl | $n_D$ 1.4795 |
| 45 | H | phenyl | —CH₃ | —CH₃ | 87–89° C./18 |
| 46 | —CHCl₂ | H | dimethylamino-ethyl | dimethylamino-ethyl | 1.4996 |
| 47 | 4-methoxy-phenyl | H | —C₂H₅ | —C₂H₅ | 263–264° C. |
| 48 | phenyl | CHCl₂ | —CH₂—CH₂— | | m.p.: 59–61° C.; 115–20° C./0.05 |
| 49 | CH₃—CH=CH— | H | —C₂H₅ | —C₂H₅ | 48–49° C./21 |
| 50 | —CHCl₂ | H | —C₂H₅ | —C₂H₅ | 107–108° C./38 |
| 51 | H | —CHCl₂ | 2-ethoxy-ethoxy-ethyl | 2-ethoxy-ethoxy-ethyl | 1.4953° C. |
| 52 | H | —CH₂Br | —CH₂—CH=CH₂ | —CH₂—CH=CH₂ | 61° C./0.5 |

TABLE I-continued

| | | | | | |
|---|---|---|---|---|---|
| 53 | H | —CHCl$_2$ | 2-ethoxy-ethyl | 2-ethoxy-ethyl | n$_D$ 1.4752 |
| 54 | —CHCl$_2$ | H | —C$_3$H$_7$ | —C$_3$H$_7$ | 210–211 |
| 55 | H | —CHCl$_2$ | —C$_{18}$H$_{37}$ | —C$_{18}$H$_{37}$ | 210° C./5 |
| 56 | H | —CHCl$_2$ | 3-methyl-n-butyl | 3-methyl-n-butyl | 62° C./1 |
| 57 | H | —CHCl$_2$ | cyclohexyl | cyclohexyl | 120° C./1 |
| 58 | —CCl$_3$ | H | H | —C$_2$H$_5$ | 183.2° C. |
| 59 | —CHCl$_2$ | H | cinnamyl | cinnamyl | n$_D$ 1.6492 |
| 60 | —CHCl$_2$ | H | —CH$_2$—CH$_2$—CH$_2$— | | 78–79° C./15 |
| 61 | —CHCl$_2$ | H | diethylamino-ethyl | diethylamino-ethyl | 1.5112 |
| 62 | H | —CHCl$_2$ | 1-methyl-n-butyl | 1-methyl-n-butyl | 58° C./1 |
| 63 | —CHCl$_2$ | H | —CH$_2$—CH$_2$—CH$_2$—CH$_2$— | | n$_D$ 1.4850 |
| 64 | H | —CHCl$_2$ | 2-cyano-ethyl | 2-cyano-ethyl | n$_D$ 1.4749 |
| 65 | H | —CHCl$_2$ | —C$_8$H$_{17}$ | —C$_8$H$_{17}$ | n$_D$ 1.4627 |
| 66 | H | —CHCl$_2$ | H | H | m.p.: 56–57° C. |
| 67 | H | —CCl$_3$ | —CH$_2$—CH$_2$— | | 198–200° C./740 |
| 68 | —CHCl$_2$ | H | —CH$_2$—CH— <br> $\quad\quad\quad\;\;$ \| <br> $\quad\quad\quad\;\;$ CH$_2$OH | | 156–7° C./19 |
| 69 | —CHBr$_2$ | H | —CH$_2$—CH$_2$— | | 102–3° C./9 |
| 70 | —CCl$_3$ | H | heptyl | heptyl | n$_D$ 1.4573 |
| 71 | —CCl$_3$ | H | α-D-glycofuranosylene | | m.p.: 182–83° C. |
| 72 | —CCl$_3$ | H | butyl | butyl | 104–5° C./3 |
| 73 | —CH$_2$Br | H | ethyl | methoxy-ethyl | 110–15° C./12 |
| 74 | —CCl$_3$ | H | allyl | H | 116° C. |
| 75 | —CH$_2$Br | H | —CH$_2$—CH$_2$— | | 172–5° C./745 |
| 76 | —CCl$_3$ | H | amyl | amyl | n$_D$ 1.4549 |
| 77 | —CCl$_3$ | H | α-D-glycofuranosylene | | m.p. 231–2° C. |
| 78 | —CCl$_3$ | H | methyl | butyl | 77–78° C./4 |
| 79 | —CH$_2$Cl | H | —CH$_2$—CH$_2$— | | 154–5° C./700 |
| 80 | —CCl$_3$ | H | —CH$_2$—CH$_2$—CH$_2$— | | 98° C./9 |
| 81 | —CCl$_3$ | H | hexyl | hexyl | n$_D$ 1.4562 |
| 82 | —CH$_2$Cl | H | methyl | methyl | 53–54° C./16 |
| 83 | —CHCl$_2$ | H | —CH$_2$—CH— <br> $\quad\quad\quad\;\;$ \| <br> $\quad\quad\quad\;\;$ CH$_2$—O—C—CH$_3$ <br> $\quad\quad\quad\quad\quad\quad\;\;$ ‖ <br> $\quad\quad\quad\quad\quad\quad\;\;$ O | | 181–83° C./19 |
| 84 | —CCl$_3$ | H | —CH$_2$—CH— <br> $\quad\quad\quad\;\;$ \| <br> $\quad\quad\quad\;\;$ CH$_2$—OCH$_3$ | | 153–5° C./18 |
| 85 | —CCl$_3$ | H | methyl | methyl | 175–6° C. |
| 86 | —CH$_2$Br | H | isopropyl | isopropyl | 53–55° C./3 |
| 87 | —CCl$_3$ | H | i-amyl | i-amyl | n$_D$ 1.4519 |
| 88 | —CCl$_3$ | H | —CH$_2$—CH— <br> $\quad\quad\quad\;\;$ \| <br> $\quad\quad\quad\;\;$ CH$_2$OH | | 162–4° C./2 |
| 89 | —CHCl$_2$ | H | —CH$_2$—CH— <br> $\quad\quad\quad\;\;$ \| <br> $\quad\quad\quad\;\;$ CH$_2$Cl | | 66° C./2 |

The antidotes according to the invention and the compositions containing them, respectively, can be prepared and used for practical purposes in any usual form. Thus emulsifiable liquids, emulsifiable concentrates, wettable powders or granular preparation can be prepared.

As active agent it is suitable to use thiocarbamate herbicides. The product containing the agent, the antidote and the carrier can be brought into the soil before or after the sowing of the seed-corns or the seeds to be sown can be treated with the product, too. Another method is to form a product suitable for the treatment of the soil or the seeds and the plants, respectively, with a corresponding liquid or solid carrier from partly the herbicidal agent, partly the protective agent according to the invention separately and they are brought into the soil successively or on the seeds, plants to be treated. That method can also be applied that the antidote of the invention is brought onto the seeds, the herbicidal agent, however, is brought before or after the sowing of the seed-corns onto the soil.

Any of the antidotes according to the invention can be used in connection with such herbicidal agents which contain the herbicidal thiocarbamates, carbamates, acid amides or urea derivatives alone or in any combination. The herbicidal activity can change in the case of the individual herbicidal agents and combinations, respectively, and can depend to a certain degree on those kinds of plants, too, on which the corresponding herbicidal compound is used alone or in a combination. With the use of any of the antidotes according to the invention in every such case protection can be reached against the activity of the chosen herbicidal agent or agent combination which would lead to a damage of the cultivated plant.

The effect of the products according to the invention were examined with seed treating and soil treating methods as follows. In the case of both methods 6 cultivated plans and 15 weed-seeds each were planted into soil filled into 10×10×10 cm plastic vessels and prepared depending on the mentioned two types of treatment and the activity of the antidotes was examined in relation to several herbicides and cultivated and weed plants, respectively, while the humidity, light and temperature were regulated.

Seed Treatment Examinations 10 g of seed-corn are shaken with 50 mg of the antidote according to the invention in a well-closing cut vessel until the substance coats the corns uniformly. The coating of the compounds onto the seeds can be furthered—if necessary—by adding acetone. The thus-pretreated seeds are put into the soil placed in the above experimental vessels to which previously the herbicidal agent was added uniformly so that in a suitable mixer a determined quantity of the herbicidal agent(s) was added to the soil from a suitably adjusted stock solution of the herbicide(s).

The seeds were put 2.5 cm deep into the prepared soil and the vessels were watered in order to ensure the positive plant growth correspondingly.

The results are summarized in Table II.

TABLE II

Damage of maize caused by herbicides (%) in the case of seeds treated with the antidote at 0.5% (A) and of untreated seeds (B)

| Number of the compound | Used herbicide Name | Quantity kg/ha | Damage of the plants after 3 weeks (%) A | B |
|---|---|---|---|---|
| 20 | Butylate | 8.1 | 5 | 48 |
| 8 | Pebulate | 5.7 | 5 | 47 |
| 27 | EPTC | 6.6 | 8 | 42 |
| 15 | EPTC | 6.6 | 13 | 52 |
| 29 | EPTC | 6.6 | 18 | 52 |
| 26 | Barban | 0.7 | 0 | 41 |
| 47 | EPTC | 6.6 | 43 | 47 |
| 65 | EPTC | 6.6 | 3 | 54 |
| 7 | EPTC | 6.6 | 12 | 43 |
| 23 | Molinate | 5.3 | 0 | 52 |
| 50 | EPTC | 6.6 | 0 | 38 |
| 36 | EPTC | 6.6 | 2 | 41 |
| 2 | Vernolate | 2.8 | 10 | 61 |
| 55 | EPTC | 6.6 | 5 | 47 |
| 11 | EPTC | 6.6 | 38 | 47 |
| 64 | EPTC | 6.6 | 0 | 41 |
| 43 | Diallate | 5.7 | 13 | 48 |
| 3 | Alachlor | 4.5 | 17 | 51 |
| 57 | Cycloate | 6.3 | 28 | 53 |
| 61 | EPTC | 6.6 | 0 | 38 |
| 59 | EPTC | 6.6 | 8 | 62 |
| 37 | Linuron | 2.2 | 30 | 54 |
| 53 | EPTC | 6.6 | 1 | 57 |
| 42 | EPTC | 6.6 | 0 | 43 |
| 52 | EPTC | 6.6 | 3 | 60 |
| 76 | Pebulate | 5.7 | 17 | 56 |
| 70 | EPTC | 6.6 | 12 | 49 |
| 87 | Butylate | 8.1 | 16 | 61 |
| 88 | Molinate | 5.3 | 13 | 53 |
| 81 | Vernolate | 2.8 | 21 | 62 |
| 68 | EPTC | 6.6 | 3 | 50 |
| 86 | EPTC | 6.6 | 18 | 39 |
| 74 | EPTC | 6.6 | 17 | 46 |
| 71 | EPTC | 6.6 | 9 | 37 |
| 77 | EPTC | 6.6 | 12 | 46 |
| 69 | EPTC | 6.6 | 8 | 37 |
| 89 | EPTC | 6.6 | 0 | 59 |

+Benthiocarb: S-(4-chlorobenzyl)-N,N-diethyl-thiocarbamide
EPTC = S-ethyl-N,N-di-n-propyl-thiocarbamate Soil Treatment Examinations In the course of these examinations the product (containing herbicidal agent and antidote) according to the invention was admixed uniformly with the soil so that corresponding quantities of the stock solution of the herbicide(s) adjusted correspondingly and of the suitably adjusted stock solution of any antidotes of the invention which were to be examined were added to the soil placed into the mixer.

Into the thus-prepared soil filled into the experimental vessels the seeds of the examined herbaceous and latifoliate cultivated plants were put 2.5 cm deep. In order to ensure the favourable growth of the plants they were watered correspondingly. The results are included in Table III.

TABLE III

Percental protection effect of antidotes against the damage of cultivated plants caused by herbicides

| Antidots Number | Quantity (kg/ha) | Herbicide Name | Quantity (kg/ha) | Cultivated plant | Protection effect (%) |
|---|---|---|---|---|---|
| 12 | 1.3 | EPTC | 6.3 | Maize | 82 |
| 25 | 3.6 | EPTC | 6.3 | Maize | 19 |
| 33 | 0.4 | EPTC | 6.3 | Maize | 100 |
| 45 | 2.1 | EPTC | 6.3 | Maize | 12 |
| 58 | 0.35 | EPTC | 6.3 | Maize | 85 |
| 24 | 1.3 | EPTC | 6.3 | Maize | 99 |
| 5 | 1.1 | EPTC | 6.3 | Maize | 82 |
| 39 | 1.6 | EPTC | 6.3 | Maize | 30 |
| 48 | 1.1 | EPTC | 6.3 | Maize | 78 |
| 63 | 0.9 | EPTC | 6.3 | Maize | 100 |
| 6 | 0.7 | Triallate$^x$ | 3.0 | Grain broom-corn | 89 |
| 22 | 1.1 | EPTC | 6.3 | Maize | 100 |
| 62 | 0.8 | EPTC | 6.3 | Maize | 100 |
| 14 | 0.8 | EPTC | 6.3 | Maize | 90 |
| 45 | 1.1 | EPTC | 6.3 | Maize | 96 |
| 1 | 0.9 | EPTC | 6.3 | Maize | 93 |
| 18 | 0.45 | Butylate | 8.9 | Maize | 97 |
| 72 | 0.35 | EPTC | 6.3 | Maize | 95 |
| 60 | 0.65 | EPTC | 6.3 | Maize | 98 |
| 30 | 2.3 | EPTC | 6.3 | Maize | 8 |
| 46 | 0.45 | EPTC | 6.3 | Maize | 97 |
| 17 | 0.4 | EPTC | 6.3 | Maize | 65 |
| 4 | 1.4 | EPTC | 6.3 | Maize | 91 |
| 19 | 0.3 | EPTC | 6.3 | Maize | 96 |
| 32 | 0.45 | EPTC | 6.3 | Maize | 93 |
| 16 | 2.7 | EPTC | 6.3 | Maize | 23 |
| 49 | 2.2 | EPTC | 6.3 | Maize | 3 |
| 83 | 1.1 | EPTC | 6.3 | Maize | 89 |
| 34 | 0.4 | EPTC | 6.3 | Maize | 92 |
| 9 | 0.3 | EPTC | 6.3 | Maize | 88 |
| 28 | 0.5 | Triallate | 8.4 | Maize | 79 |
| 66 | 1.2 | EPTC | 6.3 | Maize | 12 |
| 56 | 1.2 | EPTC | 6.3 | Maize | 100 |
| 10 | 0.9 | EPTC | 6.3 | Maize | 73 |
| 73 | 0.7 | EPTC | 6.3 | Maize | 72 |
| 54 | 0.8 | EPTC | 6.3 | Maize | 100 |
| 82 | 0.9 | EPTC | 6.3 | Maize | 90 |
| 41 | 0.45 | EPTC | 6.3 | Maize | 68 |
| 84 | 0.75 | EPTC | 6.3 | Maize | 86 |
| 13 | 3.2 | EPTC | 6.3 | Maize | 15 |
| 44 | 0.6 | EPTC | 6.3 | Maize | 98 |
| 85 | 0.75 | EPTC | 6.3 | Maize | 83 |
| 75 | 1.2 | EPTC | 6.3 | Maize | 83 |
| 51 | 1.4 | Vernolate | 6.5 | Maize | 93 |
| 31 | 3.0 | EPTC | 6.5 | Maize | 63 |
| 35 | 1.6 | EPTC | 6.5 | Maize | 95 |
| 67 | 0.25 | EPTC | 6.3 | Maize | 81 |
| 38 | 0.95 | EPTC | 6.3 | Maize | 100 |
| 80 | 0.8 | EPTC | 6.3 | Maize | 87 |
| 71 | 0.45 | EPTC | 6.3 | Maize | 77 |
| 21 | 1.2 | EPTC | 6.3 | Maize | 87 |
| 78 | 0.7 | EPTC | 6.3 | Maize | 81 |

$^x$Triallate: S-2,3,3-trichloro-allyl-N,N-diisopropyl-thiocarbamate

In both the seed treatment and the soil treatment examinations the herbicidal agent itself, combined with any antidote according to the invention, further for the phytotoxicity establishment any antidote itself were used.

The antidotes listed in Tables II and III did not decrease the weed-killing activity of the herbicidal agents beside the protection against the damage of the cultivated plants caused by herbicides.

The damage of a cultivated plant species caused by a herbicide or herbicidal combination can be prevented by any of the antidotes according to the invention. According to the invention the scope of cultivated plants protectable against the damage caused by the herbicidal agent is not restricted to the cultivated plants mentioned in the examples.

The herbicidal agents usable in combination with the antidotes according to the invention are efficacious against a wide range of plant species; optionally the quantity to be used in order to reach the desired effect depends on the kind of the expected effect and the local conditions, too.

In the products of the invention the common quantity of the herbicidal agent(s) and the antidote can be suitably 0.1 to 95 percent by weight; besides, the composition can contain solid or liquid carriers being usual in herbicidal products, e.g. kaolin, talcum and water, respectively, or organic solvents or diluents, furthermore wetting agents or emulsifying agents and other usual additives.

The following characterizing examples relate to the preparation of products ready for the suitable use of the compositions according to the invention.

EXAMPLE 39

Preparation of An Active Agent Concentrate 90 parts by weight of a herbicidal active agent, 8 parts by weight of the protective agent according to the invention and 5 parts by weight of Tween 40 emulsifier are admixed. From the thus-obtained concentrate a stable and sprayable emulsion can be prepared by dilution with a necessary quantity of a solvent e.g. toluene and water.

EXAMPLE 40

Preparation of An Emulsifiable Concentrate 10 parts by weight of a herbicidal active agent are dissolved in 25 parts by weight of xylene, then 2 parts by weight of the antidote of the invention and 4 parts by weight of an emulsifier are added. The thus-obtained concentrate supplies—diluted with water—a stable, sprayable emulsion.

EXAMPLE 41

Preparation of a Wettable Powder 15 parts by weight of an active agent, 2 parts by weight of the antidote of the invention, 50 parts by weight of kaolin and 6 parts by weight of trimethylcetyl-ammonium-bromide are admixed and ground in a ball mill. The thus-prepared wettable powder can be suspended in water and the suspension is sprayable.

What is claimed is:

1. A herbicidal composition comprising an active amide, urea, thiocarbamate, carbamate herbicide compound, and an antidotally effective amount of a heterocyclic compound having formula I:

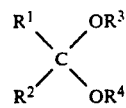

wherein
$R^1$ and $R^2$, independently of each other, are hydrogen, $C_{1-6}$ alkyl, $C_{2-6}$ alkenyl, $C_{1-4}$ cyanoalkyl, $C_{1-6}$ haloalkyl, phenyl-$C_{1-4}$-haloalkyl, phenyl, halogenphenyl, $C_{1-4}$-alkylphenyl, $C_{1-4}$-alkoxyphenyl or; and $R^3$ and $R^4$, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene or halogen-$C_3$-alkylene.

2. A herbicidal composition comprising an active thiocarbamate herbicide compound, and an antidotally effective amount of a compound of the formula I, as defined in claim 1, where $R^1$ and $R^2$, independently of each other, are hydrogen, $C_{-6}$-alkyl, $C_{2-6}$-alkenyl, $C_{1-4}$-cyanoalkyl, $C_{1-6}$-haloalkyl, phenyl-$C_{1-4}$-haloalkyl, phenyl, halogen-phenyl, $C_{1-4}$-alkylphenyl, $C_{1-4}$-alkoxyphenyl or; and $R^3$ and $R^4$, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene, halogen-$C_3$-alkylene.

3. The herbicidal composition of claim 2, where the active thiocarbamate is from the group consisting of EPTC (S-ethyl-N,N-di-n-propyl-thiocarbamate), Butylate (S-ethyl-N,N-di-isobutyl-thiocarbamate), Vernolate (S-n-propyl-N-,N-di-n-propyl-thiocarbamate), Pebulate (S-n-propyl-N-butyl-N-ethyl-thiocarbamate), Molinate (S-ethyl-N,N-hexamethylene-thiocarbamate), Cycloate (S-ethyl-N-ethyl-N-cyclohexyl-thiocarbamate), Diallate (S-2,3-dichloro-allyl-N,N-di-isopropyl-thiocarbamate), and Barban (4-chloro-2-butinyl-N(3-chlorophenyl)-carbamate).

4. A herbicidal composition comprising an active chloroacetanilide herbicide compound and an antidotally effective amount of a compound of the formula I as defined in claim 1, where $R^1$ and $R^2$, independently of each other, are hydrogen, $C_{1-6}$-alkyl, $C_{2-6}$-alkenyl, $C_{1-4}$-cyanoalkyl, $C_{1-6}$-haloalkyl, phenyl-$C_{-4}$-haloalkyl, phenyl, halogenphenyl, $C_{1-4}$-alkylphenyl, $C_{1-4}$-alkoxyphenyl; and $R^3$ and $R^4$, together, are $C_{2-4}$-alkylene, $C_4$-alkenyl, acetoxy-$C_3$-alkylene, $C_{1-4}$-alkoxy-$C_3$-alkylene, hydroxy-$C_3$-alkylene or halogen-$C_3$-alkylene.

5. The herbicidal composition of claim 4, where the active chloroacetanalide is from the group consist of Acetochlor (2-ethyl-6-methyl-N-ethoxy-methyl-chloroacetanilide), Alachlor (2,6-diethyl-N-methoxy-methyl-chloro-acetaniide), Metolachlor (6-ethyl-2-methyl-N-(2-methoxy-1-methyl-ethyl)-chloro-acetanilide).

6. A herbicidal composition comprising an active thiocarbamate herbicide compound and an antidotally effective amount of a compound of the formula I, as defined in claim 1, wherein $R^1$ is hydrogen, $C_{1-4}$-alkyl or phenyl, and $R^3$ and $R^4$, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene or halogen-$C_3$-alkylene.

7. A herbicidal composition comprising an active acetamide herbicide compound and an antidotally effective amount of a compound of the formula I, as defined in claim 1, wherein R¹ is hydrogen, $C_{1-4}$-alkyl or phenyl, R² is halogen-$C_{1-4}$-alkyl, and R³ and R⁴, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene or halogen-$C_3$-alkylene.

8. A herbicidal composition comprising an active thiocarbamate herbicide compound and an antidotally effective amount of a compound of the formula I, as defined in claim 1, wherein R¹ is hydrogen, $C_{1-4}$-alkyl or phenyl, R² is dichloromethyl, and R³ and R⁴, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene or halogen-$C_3$-alkylene.

9. A herbicidal composition comprising an active acetanilide herbicide compound and an antidotally effective amount of a compound of the formula I, as defined in claim 1, wherein R¹ is hydrogen, $C_{1-4}$-alkyl or phenyl, R² is dichloromethyl, and R³ and R⁴, together, are $C_{2-4}$-alkylene, $C_4$-alkenylene, acetoxy-$C_3$-alkylene, $C_{1-4}$-alkoxy-$C_3$-alkylene, hydroxy-$C_3$-alkylene or halogen-$C_3$-alkylene.

10. A herbicidal composition comprising an active thiocarbamate herbicide compound and an antidotally effective amount of a compound having formula I, as defined in claim 1, wherein R¹ is hydrogen, $C_{1-4}$-alkyl, phenyl, R² is dichloromethyl, R³ and R⁴ together are $C_{2-4}$-alkylene.

11. A herbicidal composition comprising an active chloroacetanilide herbicide compound and an antidotally effective amount of a compound having formula I, as defined in claim 1, wherein R¹ is hydrogen, $C_{1-4}$-alkyl, phenyl, R² is dichloromethyl, R³ and R⁴ together are $C_{2-4}$-alkylene.

12. A herbicidal composition comprising an active thiocarbamate herbicide compound and an antidotally effective amount of a compound having formula I, as defined in claim 1, wherein R¹ is hydrogen, R² is dichloromethyl, R³ and R⁴ are $C_{1-4}$-alkoxy-$C_{2-4}$-alkyl.

13. A herbicidal composition comprising an active chloroacetanilide herbicide compound and an antidotally effective amount of a compound having formula I, as defined in claim 1, wherein R¹ is hydrogen, R² is dichloromethyl, R³ and R⁴ are $C_{1-4}$-alkoxy-$C_{2-4}$-alkyl.

14. A method of selectively killing undesired weeds growing among crop plants which comprises treating crop seeds by coating them with the compound of formula I, as defined in claim 1, using acetone to aid in coating if necessary, prior to planting the seeds in soil into which herbicides had previously been incorporated.

15. A method of selectively killing undesired weeds growing among crop plants which comprises: incorporating into the soil in which the crops are to be grown or applying directly onto the weeds, a herbicidally effective amount of the composition of claim 1, which amount does not appreciably injure the crop plants.

16. The method of claim 15, wherein the composition is incorporated into the soil prior to the seeding of the soil.

17. The method of claim 15, wherein a herbicidally effective amount of the composition is incorporated in the soil after the soil has been seeded with crop seeds.

18. The method of claim 15, wherein the herbicidally active compound is S-ethyl-N,N-di-n-propyl-thiocarbamate.

19. The method of claim 15 wherein the crop plants are wheat, corn (maize), sunflower, oilseed rape, sugarbeets, barley, sorghum, rice, or soybeans.

20. The method of claim 15 wherein the crop plant is corn (maize).

21. The method of claim 15, wherein the herbicidally active compound is S-ethyl-N,N-di-n-propyl-thiocarbamate and the crop plant is corn.

22. A herbicidal composition comprising an active thiocarbamate herbicide compound and an antidotally effective amount of a compound having formula IV:

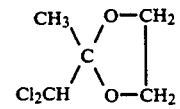

23. A herbicidal composition comprising an active chloroacetanilide herbicide compound and an antidotally effective amount of a compound having formula IV, as defined in claim 22.

24. A herbicidal composition comprising S-ethyl-N,N-dipropylthiocarbamate and an antidotally effective amount of a compound having formula IV, and defined in claim 22.

25. A herbicidal composition comprising 2-chloro-N-(2-ethyl-6-methylphenyl)-N-ethoxymethyl acetamide and an antidotally effective amount of a compound having formula IV, as defined in claim 22.

26. A herbicidal composition comprising S,N,N-tripropylthiocarbamate and an antidotally effective amount of a compound having formula IV, as defined in claim 22.

27. A herbicidal composition comprising S-ethyl-N,N-diisobutyl-thiocarbamate and an antidotally effective amount of a compound having formula IV, as defined in claim 22.

28. A herbicidal composition comprising 2-chloro-N-(2,6-diethylphenyl)-N-methoxymethyl acetamide and an antidotally effective amount of a compound having formula IV, as defined in claim 22.

29. A method of selectively killing undesired weeds growing among crop plants which comprises: incorporating into the soil in which the crops are to be grown or applying directly onto the weeds, a herbicidally effective amount of the composition of claim 23, which amount does not appreciably injure the crop plants.

30. A method of selectively killing undesired weeds growing among crop plants which comprises: incorporating into the soil in which the crops are to be grown or applying directly onto the weeds, a herbicidally effective amount of the composition of claim 24, which amount does not appreciably injure the crop plants.

31. A method of selectively killing undesired weeds growing among crop plants which comprises: incorporating into the soil in which the crops are to be grown or applying directly onto the weeds, a herbicidally effective amount of the composition of claim 22, which amount does not appreciably injure the crop plants.

32. The method of claim 31, wherein the crop plants are corn (maize), barley, rice, sunflower, sugarbeets, sorghum, soybeans, oilseed rape, or wheat.

33. The method of claim 31 wherein the crop plant is corn (maize) and the herbicidally active agent is S-ethyl-N,N-di-n-propyl-thiocarbamate.

* * * * *

UNITED STATES PATENT AND TRADEMARK OFFICE
CERTIFICATE OF CORRECTION

PATENT NO. : 5,116,402

DATED : May 26, 1992

INVENTOR(S) : DUTKA, KOMIVES, FODOR, MARTON, CSIKOS, OSZTHEIMER, HENGER LABORCZY, RETI, SEBOK, SZABOLCS, TOMORDI

It is certified that error appears in the above-identified patent and that said Letters Patent is hereby corrected as shown below:

Claim 24, col 18, line 29, delete "and" and insert therefor --as--.

Signed and Sealed this

Tenth Day of August, 1993

Attest:

MICHAEL K. KIRK

Attesting Officer

Acting Commissioner of Patents and Trademarks